United States Patent [19]

Dunmore et al.

[11] Patent Number: 4,767,860
[45] Date of Patent: Aug. 30, 1988

[54] PREPARATION OF N-SUBSTITUTED PIPERAZINONES

[75] Inventors: Gordon C. Dunmore, Fort Saskatchewan; Kevin C. Taylor, Ottawa, both of Canada; Brian W. S. Kolthammer, Lake Jackson, Tex.

[73] Assignee: The Dow Chemical Company, Midland, Mich.

[21] Appl. No.: 917,861

[22] Filed: Oct. 14, 1986

[51] Int. Cl.$^4$ .............................................. C07D 241/08
[52] U.S. Cl. .......................................... 544/384; 544/354
[58] Field of Search ................................. 544/384, 354

[56] References Cited

U.S. PATENT DOCUMENTS

| | | | |
|---|---|---|---|
| 2,649,450 | 8/1953 | Strong et al. | 544/384 |
| 2,700,668 | 1/1955 | Strong et al. | 544/384 |
| 3,056,784 | 10/1962 | Carr, Jr. et al. | 544/384 |
| 3,056,786 | 10/1962 | Phillips | 544/384 |
| 3,072,658 | 1/1963 | Fancher et al. | 544/384 |
| 3,365,453 | 1/1968 | Archer | 544/384 |
| 4,100,256 | 7/1978 | Bozzelli et al. | 423/220 |
| 4,112,049 | 9/1978 | Bozzelli et al. | 423/226 |
| 4,167,512 | 9/1979 | Lai | 544/384 |
| 4,240,961 | 12/1980 | Lai | 544/384 |
| 4,246,412 | 1/1981 | Lai | 544/384 |
| 4,292,240 | 9/1981 | Lai et al. | 544/384 |
| 4,297,497 | 10/1981 | Lai | 544/384 |
| 4,298,737 | 11/1981 | Lai et al. | 544/360 |
| 4,466,915 | 8/1984 | Lai | 544/384 |
| 4,466,916 | 8/1984 | Lai et al. | 544/384 |
| 4,521,604 | 6/1985 | Plath et al. | 544/384 |

FOREIGN PATENT DOCUMENTS 523091  9/1978  U.S.S.R. ............................. 544/384

OTHER PUBLICATIONS

Martin, Jr., et al., *J. Am. Chem. Soc.*, 72, 4301-2 (1950).

*Primary Examiner*—Glennon H. Hollrah
*Assistant Examiner*—James H. Turnipseed

[57] ABSTRACT

N-substituted piperazinones are prepared by reacting an N-substituted ethylenediamine such as N,N'-dimethylethylenediamine with a 2-oxoaldehyde such as glyoxal. N-substituted piperazinones are useful as flue gas desulfurization agents.

11 Claims, No Drawings

PREPARATION OF N-SUBSTITUTED PIPERAZINONES

BACKGROUND OF THE INVENTION

This invention relates to the preparation of N-substituted piperazinones. More specifically, it pertains to a process for preparing N-substituted piperazinones by reacting a substituted diamine with an aldehyde.

The piperazinones prepared by this invention are useful as catalysts for the hydrolysis of carbon oxysulfide which is a toxic contaminant found in petroleum refinery gases and coal gasification product streams. Piperazinones are also useful for extracting hydrogen sulfide and lower alkyl mercaptans from various industrial gas streams. Piperazinones have further been found to be powerful stabilizers for materials subject to ultraviolet light degradation.

There exists several methods for the preparation of N-substituted piperazinones. U.S. Pat. No. 2,649,450 describes a process wherein a carbonyl compound, hydrogen cyanide and an ethylenediamine are reacted in the presence of water to yield a 1,4-dialkylpiperazin-2-one. This process is disadvantageous in that it requires the use of highly toxic hydrogen cyanide. The intermediate cyanohydrin of this process is also slow to rearrange to the final product.

U.S. Pat. No. 4,167,512 describes two syntheses for preparing poly-substituted 2-keto-1,4-diazacycloalkanes. One synthesis involves reacting a 1,2-diamine with a cyanohydrin in the presence of an organic solvent, an aqueous alkali, an onium salt catalyst and a haloform. The other method disclosed in U.S. Pat. No. 4,167,512 involves reacting a 1,2-diamine with a monoketone or monoaldehyde and a haloform reactant in the presence of an organic solvent, an aqueous alkali and an onium salt catalyst. These syntheses are disadvantageous in that the intermediates produced in these syntheses require severe conditions for conversion to the desired products. Thus, these syntheses are not as economical as desired.

What is needed is a toxic-free and straightforward process for preparing N-substituted piperazinones in a high yield. Such a process would allow the efficient production of N-substituted piperazinones which are useful in the removal of toxic contaminants from various industrial gases. The piperazinones so produced could also be used as stabilizers for materials susceptible to ultraviolet light degradation.

SUMMARY OF THE INVENTION

The present invention is a facile, high yield process for the production of N-substituted piperazinones. The process of the present invention comprises contacting an N-substituted ethylenediamine with a 2-oxoaldehyde in proportions and under reaction conditions sufficient to produce an N-substituted piperazinone.

The present process avoids the use of hydrogen cyanide and proceeds rapidly under the reaction conditions described herein. The N-substituted piperazinones are produced in high yield and purity by the process of the present invention.

DETAILED DESCRIPTION OF THE INVENTION

The process of the present invention comprises contacting an N-substituted ethylenediamine and a 2-oxoaldehyde in proportions and under reaction conditions sufficient to produce an N-substituted piperazinone.

The N-substituted ethylenediamines useful in the present invention must be substituted at one of the N positions and can be substituted at the other N position and at the C position. Preferred substituted ethylenediamines of the present invention correspond to the following general formula:

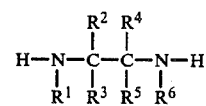

wherein $R^1$, $R^2$, $R^3$, $R^4$, $R^5$ and $R^6$ independently can be hydrogen, a hydrocarbon chain or ring of from 1 to 9 carbon atoms, aryl, arylalkyl or alkylaryl with the proviso that $R^1$ and $R^6$ cannot both be hydrogen and that $R^2$ and $R^4$ and/or $R^3$ and $R^5$ in combination with the ethylene moiety to which $R^2$, $R^4$, $R^3$ and $R^5$ are bonded can form a hydrocarbon ring of from 5 to 7 carbon atoms.

Preferred substituted ethylenediamines include N-methylethylenediamine, N-ethylethylenediamine, N,N'-dimethylethylenediamine, N,N'-diethylethylenediamine, N,N'-di(n-propyl)ethylenediamine, N,N'-di(n-butyl)ethylenediamine, N,N'-di(t-butyl)ethylenediamine, and N,N'-dihexylethylenediamine. N,N'-dimethylethylenediamine is the most preferred ethylenediamine.

Any 2-oxoaldehyde which will react sufficiently with an N-substituted ethylenediamine of the present invention to form an N-substituted piperazinone can be utilized in the present process. Preferred 2-oxoaldehydes of this invention correspond to the following general formula:

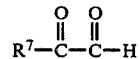

wherein $R^7$ can be hydrogen or a hydrocarbon chain or ring of from 1 to 9 carbon atoms, aryl, arylalkyl or alkylaryl, with the 2-oxoaldehydes wherein $R^7$ is alkyl or hydrogen being more preferred.

Examples of more preferred 2-oxoaldehydes include glyoxal, methylglyoxal, ethylglyoxal and propylglyoxal. Glyoxal is the most preferred.

The 2-oxoaldehyde may be employed in any amount sufficient to react with the N-substituted ethylenediamine such that the desired N-substituted piperazinone is produced. The molar ratio of 2-oxoaldehyde to N-substituted ethylenediamine is preferably in the range from about 1 to about 5, more preferably from about 1 to about 2 and most preferably is about 1.1.

Although not required, a solvent is advantageously employed in the practice of the present invention. An solvent which will dissolve both reactants can be utilized in the practice of the present invention. Typical solvents include ethers such as diethyl ether, alcohols such as methanol and ethanol, and water with water and methanol being preferred. Water is the most preferred solvent.

Any amount of solvent sufficient to dilute the reactants to allow bimolecular cyclization to occur preferentially can be utilized in the present process. Preferred molar ratios of solvent to N-substituted ethylenediamine are in the range from about 50 to about 1000, more preferably from about 100 to about 200, with 150 being most preferred.

The reaction can be carried out at any temperature and pressure sufficient to form the N-substituted piperazinone. Suitable temperatures are in the range from about 50° C. to about 110° C., preferably from about 90° C. to about 100° C. Sub- or super-atmospheric pressures can be utilized with ambient pressure being preferred for convenience.

The product can be separated by well-known distillation techniques and is advantageously produced in yields greater than about 30 percent, preferably greater than 90 percent.

The process of the present invention can be represented by the following general scheme

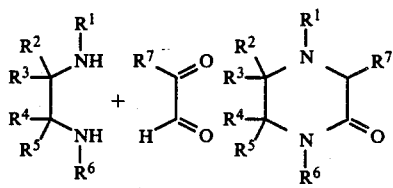

wherein $R^1$-$R^7$ are as defined hereinbefore.

N-substituted piperazinones prepared by this invention include 1,4-dimethylpiperazin-2-one, 1,4-diethylpiperazin-2-one, 1,4-di(n-propyl)piperazin-2-one, 1,4-di(n-butyl)piperazin-2-one and 4-methylpiperazin-2-one and 1,3,4-trimethylpiperazin-2-one.

SPECIFIC EMBODIMENTS

The following examples are given for illustrative purposes only and are not intended to limit the scope of the claims. All parts and percentages are by weight unless otherwise indicated.

EXAMPLE 1

To 10 g (69.0 mmoles) of 40 percent glyoxal and 200 ml of distilled water is rapidly added 6.1 g (69.0 mmoles) of N,N'-dimethylethylenediamine. The solution is heated rapidly to reflux and heating maintained for 5 minutes. The dark brown solution is allowed to cool to room temperature and is then evaporated at 60° C. under water pump vacuum to a viscous brown oil. The oil is distilled in a short path distillation apparatus to yield 8.2 g (93 percent yield) of 1,4-dimethylpiperazin-2-one in the form of a yellow oil. Purity is greater than 99 percent by capillary gas chromatograph.

EXAMPLE 2

To 10.0 g (69.0 mmoles) of 40 percent glyoxal and 200 ml of distilled water is rapidly added 8.0 g (69.0 mmoles) of N,N'-diethylethylenediamine. The solution is heated rapidly to reflux and heating maintained for 5 minutes. The dark brown solution is allowed to cool to room temperature and is then evaporated at 60° C. under water pump vacuum to a viscous brown oil. The oil is distilled in a short path distillation apparatus to yield 10 g (93 percent yield) of 1,4-diethylpiperazin-2-one in the form of a yellow oil. Purity is greater than 99 percent by capillary gas chromatograph.

EXAMPLE 3

To 10.0 g (69.0 mmoles) of 40 percent glyoxal and 200 ml of distilled water is rapidly added 9.94 g (69.0 mmoles) of N,N'-di(n-propyl)ethylenediamine. The solution is heated rapidly to reflux and heating maintained for 5 minutes. The dark brown solution is allowed to cool to room temperature and is then evaporated at 60° C. under water pump vacuum to a viscous brown oil. The oil is distilled in a short path distillation apparatus to yield 9.3 g (73 percent yield) of a yellow oil. Purity is greater than 99 percent of 1,4-di(n-propyl)-piperazin-2-one as determined by capillary gas chromatograph.

EXAMPLE 4

To 10 g (69.0 mmoles) of 40 percent glyoxal and 200 ml of methanol is rapidly added 11.9 g (69.0 mmoles) of N,N'-di(n-butyl)ethylenediamine. The solution is rapidly brought to reflux and heating is maintained for 5 minutes. The dark brown solution is then allowed to cool to room temperature at which time fine white crystals precipitate from the brown oil. The oil is diluted with 100 ml of 1,4-dioxane and the solid is removed by filtration. The dioxane solution is concentrated under aspirator vacuum and distilled in a short path distillation apparatus to give 4.5 g of 1,4-di(n-butyl)piperazin-2-one in the form of a brown oil (31 percent yield).

EXAMPLE 5

To 10.0 g (69.0 mmoles) of 40 percent glyoxal and 200 ml of distilled water is rapidly added 5.0 g (69.0 mmoles) of N-methylethylenediamine. The solution is heated rapidly to reflux and heating maintained for 5 minutes. The dark brown solution is allowed to cool to room temperature and is then evaporated at 60° C. under water pump vacuum. After removal of water, 3.62 g (46 percent yield) of 4-methyl-2-piperazinone (yellow crystals) are obtained by vacuum sublimation. Purity is greater than 99 percent by capillary gas chromatograph.

What is claimed is:

1. A process comprising contacting an N-substituted ethylenediamine with a 2-oxoaldehyde in proportions and under reaction conditions sufficient to form an N-substituted piperazinone.

2. The process of claim 1 wherein the N-substituted ethylenediamine corresponds to the following general formula:

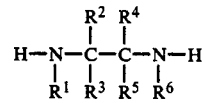

wherein $R^1$, $R^2$, $R^3$, $R^4$, $R^5$ and $R^6$ independently can be hydrogen, a hydrocarbon chain or ring of from 1 to 9 carbon atoms, aryl, arylalkyl or alkylaryl with the proviso that $R^1$ and $R^6$ cannot both be hydrogen and that $R^2$ and $R^4$ and/or $R^3$ and $R^5$ when taken in combination with the ethylene moiety to which $R^2$, $R^4$, $R^3$ and $R^5$ are bonded can form a hydrocarbon ring of from 5 to 7 carbon atoms.

3. The process of claim 2 wherein the 2-oxoaldehyde corresponds to the following general formula:

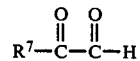

wherein $R^7$ can be hydrogen or a hydrocarbon chain or ring of from 1 to 9 carbon atoms, aryl, arylalkyl or alkylaryl.

4. The process of claim 3 wherein the substituted ethylenediamine is N,N'-diethylethylenediamine.

5. The process of claim 4 wherein the substituted ethylenediamine is N,N'-dimethylethylenediamine.

6. The process of claim 5 wherein the 2-oxoaldehyde is pyruvic aldehyde.

7. The process of claim 6 wherein the 2-oxoaldehyde is glyoxal.

8. The process of claim 7 wherein the solvent is water.

9. The process of claim 8 wherein the solvent is methanol.

10. A process comprising contacting a substituted ethylenediamine with a 2-oxoaldehyde in a polar solvent at a reflux temperature for a sufficient period of time to form an N-substituted piperazinone.

11. A process for preparing 1,4-dimethylpiperazin-2-one comprising (1) contacting an aqueous solution of glyoxal with N,N'-dimethylethylenediamine, (2) heating the mixture of (1) to a reflux temperature and maintaining reflux for 5 minutes, and (3) cooling the reaction mixture and recovering the product by distillation.

* * * * *